United States Patent [19]
Sibi et al.

[11] Patent Number: 5,623,087
[45] Date of Patent: Apr. 22, 1997

[54] METHOD FOR PREPARATION OF OPTICALLY ACTIVE DIARYLALANINES

[75] Inventors: Mukund P. Sibi; Prasad K. Despande; Anthony J. LaLoggia, all of Fargo, N. Dak.

[73] Assignee: NDSU-Research Foundation, Fargo, N. Dak.

[21] Appl. No.: 410,861

[22] Filed: Mar. 10, 1995

[51] Int. Cl.$^6$ .................................................. C07C 229/00
[52] U.S. Cl. .............................. 562/576; 560/8; 560/123; 560/124; 560/129; 564/323; 564/192; 564/161
[58] Field of Search ............................... 560/8, 123, 124, 560/129; 564/161, 189, 192, 323; 562/576

[56] References Cited

U.S. PATENT DOCUMENTS

| | | |
|---|---|---|
| 4,766,109 | 8/1988 | Czarniecki et al. . |
| 5,198,548 | 3/1993 | Beylin et al. . |
| 5,264,577 | 11/1993 | Beylin et al. . |

FOREIGN PATENT DOCUMENTS 0522808  1/1993  European Pat. Off. .

OTHER PUBLICATIONS

Journal of Organic Chemistry, 1976, 41 (19) 3219–20 . . . Hansen, John F.; Sep. 17, 1976.
Tetrahedron Letters, 1995, 36(31)5619–5622 . . . Koskinen, Ari M.P. et al.
Beaulieu, et al., "Enantiospecific Synthesis of D–α,ω–Diaminoalkanoic Acids", *Tetrahedron Letters*, 29: 2019–2022 (1988).
Beaulieu, et al., "Synthesis of Chiral Vinylglycines", *J. Org. Chem.*, 56: 4196–4204 (1991).
Bertozzi, et al., "Synthesis of Carbon–Linked Glycopeptides as Stable Glycopeptide Models", *J. Org. Chem.*, 57: 6092–6094 (1992).
Beylin et al., "Cyclic Derivatives of 3,3–Diphenylalanine (DIP) (II), Novel α–Amino Acids for Peptides of Biological Interest", *Tetrahedron Letters*, 34: 953–956 (1993).
Burckhalter et al., "Synthesis of Phenylalanine Analogs as Antimetabolites", *J. Am. Chem. Soc.*, 73: 56–58 (1951).
Burgess, et al., "Asymmetric Syntheses of Optically Active α,β–Disubstituted β–Amino Acids", *J. Org. Chem.*, 58: 4758–4763 (1993).
Chassaing, et al., "Synthesis of conformationally constrained phenylalanines and their incorporation into tachykinins", *Peptides Chemistry, Structure and Biology*, Proceedings of the Eleventh American Peptide Symposium, pp. 935–936 (1989).
Chen, et al., "Chiral Synthesis of D–and L–3,3–Diphenylalanine (DIP), Unusual α–Amino Acids for Peptides of Biological Interest", *Tetrahedron Letters*, 33: 3293–3296 (1992).
Evans, et al., "Asymmetric Alkylation Reactions of Chiral Imide Enolates. A Practical Approach to the Enantioselective Synthesis of α–Substituted Carboxylic Acid Derivatives", *J. Am. Chem. Soc.*, 104: 1737–1739 (1982).

Evans, et al., "The Asymmetric Synthesis of α–Amino Acids, Electrophilic Azidation of Chiral Imide Enolates, a Practical Approach to the Synthesis of (R)–and (S)–α–Azido Carboxylic Acids", *J. Am. Chem. Soc.*, 112: 4011–4030 (1990).
Filler, et al., "A New Synthesis of β,β–Diphenylalanine and Related Unnatural α–Amino Acids", *J. Org. Chem.*, 26: 1685 (1961).
Filler, et al., "Synthetic Routes to β,β–Diaryl–α–Amino Acids via Nitrogen Heterocycles (1)", *J. Het. Chem.*, 1: 153–157 (1964).
Gage, et al., "Diastereoselective Aldol Condensation Using a Chiral Oxazolidnone Auxiliary: (2S*, 3S*)–3—Hydroxy–3–Phenyl–2–Methylpropanoic Acid", *Organic Synthesis*, 68: 83–89 (1989).
Goodson, et al., "Potential Growth Antagonists. I. Hydrantoins and Disubstituted Glycines", *J. Org. Chem.*, 25: 1920–1924 (1960).
Hsieh, et al., "Topographic Probes of Angiotensin and Receptor: Potent Angiotensin II Agonist Containing Diphenylalanine and Long–Acting Antagonists Containing Biphenylalanine and 2–Indan Amino Acid in Position", *J. Med. Chem.*, 32: 898–903 (1989).
Josien, et al., "Asymmetric Synthesis of L–Diphenylalanine and L–9–Fluorenylglycine via Room Temperature Alkylations of a Sultam–Derived Glycine Imine", *Tetrahedron Letters*, 32: 6547–6550 (1991).
Kanemasa, et al., "New Chiral Auxiliaries Based on Conformation Control, a $C_2$–Symmetric 2,2–Dimethylimidazolidine and 4–Chiral 2,2–Dialkyloxazolidines. Synthesis and Conformational Analysis of Acrylamides Derivatives", *Tetrahedron*, 48: 8631–8644 (1992).
Krysin, et al., "Electrochemical Synthesis of α–Amino Acids", *Soviet Electrochemistry*, 12: 1449–1451 (1976).
Luly, et al., "A Synthesis of Protected Aminoalkyl Expoxides from α–Amino Acids", *J. Org. Chem.*, 52: 1487–1492 (1987).
Mustafa, et al., "Action of Grignard Reagents. XXII. Action of Organomagnesium Compounds on 2–Mercapto–4–arylidene–5–thiazolidones and on 4–Arylidene–2,5–thiazolidinediones. Reaction of 2–Mercapto–4–benzylidene–5–thiazolidone with Diazomethane", *J. Org. Chem.*, 26: 1782–1786 (1961).
O'Donnell, et al., "The Stereoselective Synthesis of α–Amino Acids by Phase–Transfer Catalysis", *J. Am. Chem. Soc.*, 111: 2353–2355 (1989).
Sasaki, et al., "Stereoselective Synthesis of Optically Pure β,γ–Unsaturated α–Amino Acids in Both L and D Configurations", *Tetrahedron Letters*, 30: 1943–1946 (1989).
Shimamoto, et al., "A New Entry to the Synthesis of β–Hydroxytyrosines Via A Novel Benzylic Hydroxylation", *Tetrahedron Letters*, 29: 5177–5180 (1988).

*Primary Examiner*—Gary Geist
*Assistant Examiner*—Sreeni Padmanabhan
*Attorney, Agent, or Firm*—Merchant & Gould, Smith, Edell, Welter & Schmidt

[57] ABSTRACT

A method for preparing a diarylalanine compound is provided. The method includes reacting a diarylaminopropanediol with a reducing agent to form a diarylaminopropanol compound and/or contacting a serine ester derivative with an aryl metal reagent to form diarylaminopropanediol. A diarylmethyloxazolidinone compound is also provided.

26 Claims, No Drawings

METHOD FOR PREPARATION OF OPTICALLY ACTIVE DIARYLALANINES

BACKGROUND OF THE INVENTION

Bulky unnatural amino acids, such as diarylalanines, are of interest since these compounds may serve as surrogates for their natural counterparts. Since the aromatic rings of phenylalanine and tyrosine amino acid residues often play important roles in peptide-receptor interactions, replacement of one of these residues with a bulky diarylalanine residue, e.g., diphenylalanine, has the potential to dramatically enhance the therapeutic activity of peptide analogs. Incorporation of a diarylalanine into a bioactive peptide may also impart biostability by inhibiting degradation by peptidases and/or provide conformational restriction. Either effect can serve to increase the pharmacological activity of a polypeptide and increase its potential as a therapeutic agent. For example, a peptidyl antagonist which incorporates an optically active form of a diarylalanine, the D-enantiomer of diphenylalanine (D-DIP), is known to be a potent antagonist of the endothelin $ET_A$ and $ET_B$ receptors. A number of luteinizing hormone-releasing hormone analogs containing various hydrophobic unnatural amino acid substitutions have been reported to have potent biological activity. Hydrophobic peptides which include a 3,3-diphenylalanine residue have been reported to have antihypertensive activity.

A series of angiotensin II analogs in which the phenylalanine at the 8-position was replaced with various unnatural amino acids including 3,3-diphenylalanine have also been described. The authors of this study indicated that they were unable to resolve the 3,3-diphenylalanine enzymatically using either carboxypeptidase or hog kidney acylase. In order to obtain the desired angiotensin II analog it was necessary to separate via countercurrent distribution the diastereomeric peptides which had been prepared from racemic 3,3-diphenylalanine. While this permitted the desired analog to be obtained, the approach was extremely inefficient since half of the product produced was the undesired diastereomer.

In order for unnatural amino acids such as diphenylalanine to become effective building blocks for the design of peptide analogs, methods which permit the unnatural amino acids to be readily prepared in high yield and in optically active form must be available.

A number of preparations of diphenylalanine (DIP) in racemic form have been reported. The unnatural amino acid has been prepared through alkylation of an acetamidomalonate ester or a hindered imine of a substituted glycinamide. A derivative of DIP has also been produced through an azide addition to a 3,3-diphenylpropionamide. Other routes, such as the alkylation and subsequent reduction of a nitroacetic acid ester are also known. These routes have not provided access to the optically active forms of DIP, nor have they facilitated the preparation of a wide variety of analogs with differing aryl groups.

Several unsuccessful attempts to resolve diphenylalanine by enzymatic resolution of a racemic derivative have been reported. These include unsuccessful attempts to selectively hydrolyse N-BOC diphenylalanine using papain or α-chymotrypsin. An effort to selectively hydrolyse N-acetyl DIP using hog kidney acylase or carboxypeptidase was also reported to be unsuccessful.

Both the D- and L- isomers of DIP have been obtained from the racemate by conventional resolution using cinchona alkaloids. This technique however, which requires the repeated recrystallization of an alkaloid salt, is not especially attractive for the preparation of large quantities of the unnatural amino acid.

More recently, there have been several reports of the preparation of DIP via asymmetric synthesis. These reports include asymmetric alkylation of a sultam-derived glycine imine, stereoselective alkylation of a hindered glycine imine in the presence of a cinchona-based phase transfer catalyst, and asymmetric azide addition to a 3,3-diphenylpropionamide using chiral auxiliary methodology. The chiral auxiliary based methods require extra steps for the introduction and cleavage of the chiral auxiliary, which is typically incorporated into a precursor as part of an amide derivative. As with the chiral phase transfer method, the chiral auxiliary methods include a purification step to remove the agent which confers chirality.

All of the methods described above suffer from one or more of a number of disadvantages—low yields, general difficulty in scaling up the procedure, use of costly reagents, inclusion of extra reaction or purification steps to introduce and/or remove a chiral agent, and the inability to alter the preparation to provide a variety of related derivatives. Accordingly, in view of the potential utility of diarylalanines in the preparation of peptide analogs and other compounds of pharmaceutical interest, there is a continuing need for methods which would permit the efficient, large scale preparation of a variety of diarylalanines and if desired, in optically active form.

SUMMARY OF THE INVENTION

The present invention provides a method for preparing a diarylalanine compound, such as diphenylalanine. The method provides a short and high yielding synthesis of the diarylalanine from readily available serine alkyl esters. The method uses commonly available reagents and is amenable to large scale synthesis. Moreover, the present method permits the chiral synthesis of diarylalanines in excellent optical purity from chiral serine alkyl esters. For example, using the present method, (R)-diphenylalanine (D-diphenylalanine) may be efficiently prepared in excellent optical purity starting from the hydrochloride salt of (S)-serine methyl ester (L-serine methyl ester). The present method also allows the synthesis of a wide variety of other unnatural aromatic amino acids by simply varying the aryl metal reagent which is used in one of the steps.

One embodiment of the method includes reacting a diarylaminopropanediol with a reducing agent to form a diarylaminopropanol compound. Another embodiment of the method includes contacting a protected serine ester compound with an aryl metal reagent to form a protected diarylaminopropanediol compound. A third embodiment of the present method includes contacting a serine ester hydrochloride compound with an aryl metal reagent to form a diarylaminopropanediol compound.

The present invention is also directed to a protected diarylaminopropanediol compound represented by the formula:

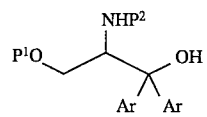

In addition, the present invention provides a diarylmethyloxazolidinone compound represented by the formula:

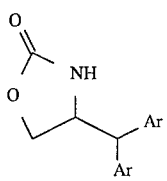

The present invention also provides a method for preparing a diarylmethyloxazolidinone compound which includes reacting a diarylhydroxymethyloxazolidinone compound with a reducing agent.

DETAILED DESCRIPTION OF THE INVENTION

The present invention provides a method which includes the step of reacting a diarylaminopropanediol compound represented by the formula:

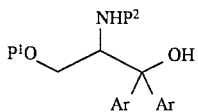

with a reducing agent to form a diarylaminopropanol compound represented by the formula:

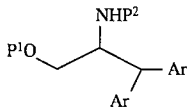

The step may be used for the preparation of the diarylaminopropanol compound or may be employed as a step in a process of producing a diarylalanine. For the purposes of this invention, the term "diarylalanine" includes the free form of the amino acid as well as salts and N-protected derivatives thereof. The Ar is a substituted or unsubstituted aromatic group, e.g., phenyl or naphthyl. $P^1$ and $P^2$ are hydrogen or any of a wide variety of standard protecting groups known to be used for the protection of alcohols or amine may be employed. Typically, $P^1$ and $P^2$ are independently hydrogen, —$C(O)R^1$, or —$C(O)OR^2$, where $R^1$ and $R^2$ are each an alkyl, cycloalkyl, phenyl, arylalkyl, fluorenyl or allyl group. The $R^1$ and $R^2$ groups may be substituted with one or more substituents such as a halogen atom, an alkyl group or an alkoxy group. $P^1$ and $P^2$ may also both be part of a single protecting group which forms a ring (e.g., where $P^1$ and $P^2$ together are >C=O). Typically, $P^1$ and/or $P^2$ are chosen to be protecting groups which are not cleaved and are substantially unreactive under the conditions of the particular step to which the protected amine and/or alcohol is to be subjected. The protecting groups may be removed and/or switched to improve the compatibility of a protected derivative with particular reaction conditions. Preferably, the same protecting group is employed throughout as much of the reaction sequence as possible. This obviates the need to include additional steps directed solely to the removal or introduction of a protecting group and enhances the overall efficiency of the sequence.

Examples of suitable alcohol protecting groups, $P^1$, include —$C(O)R^1$, where $R^1$ is a substituted or unsubstituted $C_1$–$C_{10}$ alkyl group, a substituted or unsubstituted $C_1$–$C_7$ cycloalkyl group, a substituted or unsubstituted arylalkyl group, or a substituted or unsubstituted phenyl group. Among preferred $P^1$ groups are acetyl ($CH_3C(O)$—) and propionyl. Depending on the reaction conditions, the alcohol group may be left unprotected, i.e., $P^1$ is hydrogen.

$P^2$ is typically hydrogen, an amide group (—$C(O)R^2$), or a carbamate group (—$C(O)OR^3$). If $P^2$ is an amide group, $R^2$ may be hydrogen, a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group. If $P^2$ is an amide group, $R^3$ may be a substituted or unsubstituted $C_1$–$C_{10}$ alkyl group, a substituted or unsubstituted $C_3$–$C_7$ cycloalkyl group, a substituted or unsubstituted arylalkyl group (e.g., benzyl), a substituted or unsubstituted phenyl group, a substituted or unsubstituted fluorenyl group, a substituted or unsubstituted allyl group. Examples of preferred $P^2$ groups include acetyl, propionyl, carbobenzyloxy (CBZ), tertiary butoxycarbonyl (BOC), fluorenylmethoxycarbonyl (FMOC), ethoxycarbonyl and methoxycarbonyl.

In addition, $P^1$ and $P^2$ may be joined together to form a ring with the amino alcohol. For example, $P^1$ and $P^2$ together may be >C=O, so that the amino and alcohol groups are protected as part of an oxazolidinone ring.

The protecting groups $P^1$ and $P^2$ are typically unsubstituted. However, in some instances substituted protecting groups of the types listed above may be employed in order to modify the reactivity of a particular protecting group. A large number of substituted and unsubstituted protecting groups for alcohols and/or amines together with methods for their preparation and removal are described in *Protective Groups in Organic Synthesis*, Greene, ed., John Wiley & Sons, New York (1981) and *Protecting Groups*, Kocienski, Thieme, Stuttgart (1994), the disclosure of which are incorporated by reference.

The present method may be employed to prepare a wide variety of diarylalanine compounds. For the purposes of this invention, the term "diarylalanine compound" include the parent amino acid as well as salts thereof and N-protected derivatives (e.g., N-BOC-diarylalanine, N-FMOC-diarylalanine and N-acetyldiarylalanine). Suitable aryl groups include any aromatic group for which a corresponding aryl Grignard reagent or aryl lithium reagent may be prepared. Examples of suitable aryl groups include aromatic hydrocarbons such as a phenyl group or a naphthyl group, as well as aromatic heterocyclic groups such as a pyridine group or a furan group. The aromatic group may optionally be substituted with one or more substituents so long as the substituents are substantially inert to the reaction conditions of the present method. Typical substituents include fluorine, chlorine, alkyl groups having from 1 to 10 carbon atoms (e.g., methyl or ethyl), alkoxy groups having from 1 to 10 carbon atoms (e.g., methoxy or ethoxy), alkoxyalkyl groups having from 1 to 10 carbon atoms and one or more oxygen atoms, or amido groups having from 1 to 10 carbon atoms, such as acetamido. The substituent(s) may also be a fluorinated alkyl group having from 1 to 10 carbon atoms (e.g., trifluoromethyl) or a fluorinated alkoxy groups having from 1 to 10 carbon atoms (e.g., trifluoromethoxy). Preferably the aromatic groups are a phenyl group or a naphthyl group which are either unsubstituted or are substituted with fluorine, a lower alkyl group (having from 1 to 6 carbon atoms), a lower alkoxy group (having from 1 to 6 carbon atoms), or trifluoromethyl.

Scheme 1

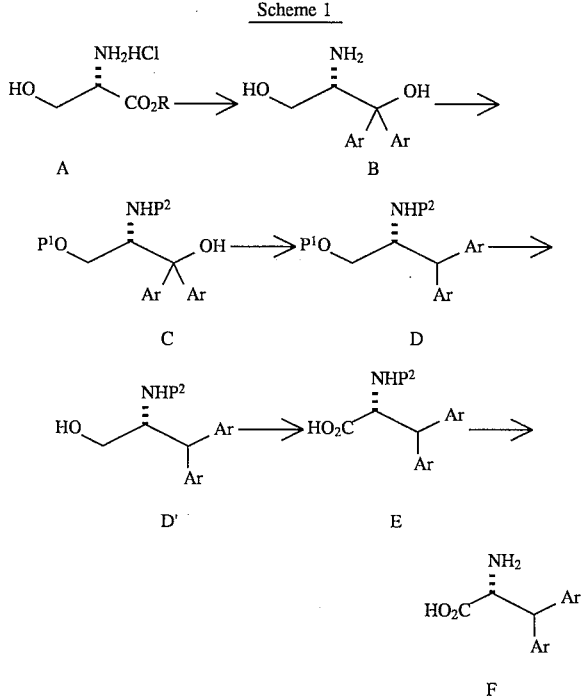

Scheme 1 depicts one embodiment of the present method for preparing a diarylalanine compound. The synthetic route shown in Scheme 1 allows the preparation of a diphenylalanine in six steps from the hydrochloride salt of a serine ester. The embodiment includes the reaction of diarylaminopropanediol compound C with a reducing agent to form diarylaminopropanol compound D. The method may also include the reaction of an aryl metal reagent, such as a phenyl magnesium halide or an aryl lithium reagent, with the serine ester hydrochloride. The serine ester typically includes an alkyl group having from 1 to 10 carbon atoms or arylalkyl group having from 5 to 12 carbon atoms. Preferably, the ester group is methyl, ethyl or benzyl.

In the sequence shown in Scheme 1, the reaction of the serine ester hydrochloride A with an aryl metal reagent produces diarylaminopropanediol B. As discussed above the aryl metal reagent may be a Grignard reagent (e.g., PhMgBr and or a substituted analog) or an aryl lithium reagent such as phenyl lithium or naphthyl lithium. The aryl metal addition is typically run in an ether solvent such as diethyl ether, dimethoxyethane or tetrahydrofuran.

Diarylaminopropanediol B may then be reacted with a derivatizing agent to form protected diarylaminopropanediol C. The particular protecting group and the conditions used to prepare the protected diarylaminopropanediol C may be chosen from a wide variety of standard protecting groups and techniques for preparing the protected diarylaminopropanediol.

Protected diarylaminopropanediol C may then be reacted with a reducing agent to form diarylaminopropanol D. A variety of reducing agents may be used to carry out the deoxygenation reaction. For example, the deoxygenation may be achieved using a dissolving metal reducing agent, such as an alkali metal or alkaline earth metal. Preferably the dissolving metal reagent is an alkali metal such as sodium or lithium and the reaction is run in the presence of liquid ammonia. When sodium is used as the reducing agent, tetrahydrofuran may also be employed as a cosolvent. Suitable conditions for the deoxygenation reaction also include the use of a hydrogen source (e.g., hydrogen ($H_2$), ammonium formate or sodium borohydride) in the presence of a noble metal catalyst such as palladium, platinum or rhodium. The noble metal catalyst is typically employed on a support such as carbon. In a preferred embodiment, the deoxygenation is run utilizing hydrogen or ammonium formate as the hydrogen source in the presence of a palladium catalyst (e.g., palladium on a carbon support).

The deoxygenation reaction may also be carried out using any of a number of other common reducing agents. Included among suitable common reducing agents which may be employed are sodium borohydride (in the presence of trifluoroacetic acid), triethylsilane (in the presence of trifluoroacetic acid), red phosphorus (in the presence of iodine and acetic acid), lithium borohydride (in the presence of aluminum chloride) and metallic tin (in the presence of hydrochloric acid and acetic acid). The deoxygenation may also be run with raney nickel as the reducing agent in the presence of a suitable solvent such as an alcohol or an ether.

The preparation of the diarylalanine is completed through the oxidation of N-protected diarylaminopropanol D' with an oxidizing agent. In order for the oxidation step to be carried, $P^1$ must be hydrogen and $P^2$ must be a protecting group which is stable under the oxidation conditions. Diarylaminopropanol D may already include an appropriate N-protecting group. Alternatively, a different protecting group may be need to be introduced or substituted onto the nitrogen atom. Where $P^1$ is not hydrogen, the selective removal of the O-protecting group may be carried out to form N-protected diarylaminopropanol D'.

The N-protected alcohol D' may be oxidized under standard oxidation conditions to produce N-protected diarylalanine E. Finally, if desired, the N-protecting group may be removed by treating N-protected diarylalanine E with a deprotecting agent to obtain diarylalanine F.

A variety of conditions are suitable for carrying out the oxidation step. Typically, the oxidation step is carried out using a chromium-based oxidizing agent such as Jones reagent ($CrO_3/H_2SO_4$). Oxygen ($O_2$) in the presence of a platinum catalyst (e.g., $PtO_2$) may also be used to effect the transformation of diarylaminopropanol D' to diarylalanine E.

One of the major advantages of the synthetic route shown in Scheme 1 is that it can be carried out with substantially no racemization at the amino-bearing chiral center. This permits either (R)- or (S)-diarylalanine to be produced by selecting (S)-serine or (R)-serine as the respective starting material. The synthetic sequence depicted in Scheme 1 shows the preparation of (R)-diphenylalanine starting from an ester of (S)-serine. Diarylalanine of greater than about 70% and preferably greater than about 95% optical purity can be prepared by the present method, i.e., the overall retention of optical activity over the entire sequence is typically at least about 70%.

Scheme 2

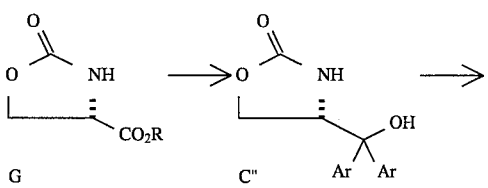

-continued
Scheme 2

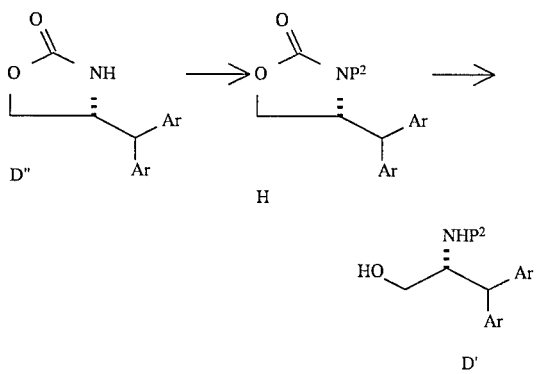

Oxazolidinone G is readily available, for example from the reaction of a serine ester with phosgene or a dialkyl carbonate. As with the starting ester in Scheme 1, the ester group "R" is typically an alkyl group having from 1 to 10 carbon atoms or arylalkyl group having from 5 to 12 carbon atoms. Preferably, the ester group is methyl, ethyl or benzyl. As with the synthetic route shown in Scheme 1, oxazolidinone G may be in either racemic or optically active form. The use of an optically active oxazolidinone (derived from either (R)- or (S)-serine) results in the production of an N-protected diarylaminopropanol D' having an optical purity comparable to the starting oxazolidinone.

Oxazolidinone G may be reacted with an aryl metal reagent to form diarylhydroxymethyl oxazolidinone C". In this second step, the presence of the acidic hydrogen atom on the nitrogen of the oxazolidinone ring is thought to protect the adjacent chiral center from racemization. Oxazolidinone C" represents an embodiment of the protected diarylaminopropanediol C (see Scheme 1) in which the carbonyl group acts as a protecting group for both the alcohol and the amine. As with the corresponding reaction in Scheme 1, the aryl metal reagent may be an aryl magnesium halide (Grignard reagent, where the halide is not fluorine) or an aryl lithium reagent. Preferably the aryl metal reagent includes a phenyl magnesium halide, where the phenyl group may be substituted with one or more substituents selected from among methyl, ethyl, methoxy, ethoxy, fluorine, chlorine, trifluoromethoxy and trifluoromethyl. The aryl magnesium halide is preferably a substituted or unsubstituted aryl magnesium bromide.

The deoxygenation step which converts oxazolidinone C" into oxazolidinone D" may be carried out under the conditions described above for the transformation of diarylaminopropanediol C to diarylaminopropanol compound D. The same types of reducing agents and conditions may be used. Preferably, the deoxygenation is carried out by treating diarylaminopropanediol C with a dissolving metal reagent in the presence of liquid ammonia. More preferably, the dissolving metal reagent includes an alkali metal such as sodium or lithium. The deoxygenation may also be carried out by reacting oxazolidinone C" with a hydrogen source in the presence of a noble metal catalyst. If this approach is utilized, the deoxygenation is typically carried out by reacting oxazolidinone C" with hydrogen or ammonium formate in the presence of a palladium, platinum or rhodium catalyst. The noble metal catalyst preferably includes palladium. Most preferably, the deoxygenation is carried out by treating the diarylaminopropanediol with sodium or lithium in the presence of liquid ammonia.

Oxazolidinone C" may be converted into the N-protected diarylaminopropanol D' through a two step process. Oxazolidinone C" may be reacted with a protecting agent (e.g., BOC-anhydride) in the presence of a base, such as a trialkylamine, sodium carbonate or potassium carbonate, to form the N-protected oxazolidinone H. Oxazolidinone H may then be selectively ring opened to N-protected diarylaminopropanol D' by treatment with cesium carbonate in an alcohol solvent such as methanol.

Oxazolidinone D", which is produced as an intermediate in the course of the approach shown in Scheme 2, may be used as a chiral auxiliary to facilitate the preparation of optically active products from racemic or achiral starting materials. This type of technique is well known and related substituted oxazolidinones have been utilized to prepare carboxylic acid derivatives which can be stereoselectively alkylated (see e.g., Evans et al., JACS, 104, 1737 (1990); Evans et al., JACS, 112, 4011 (1989); and Beylin et al., Tett. Letters, 953 (1993)).

Scheme 3 depicts another embodiment of the invention which allows the preparation N-protected diarylaminopropanol D' starting from N-protected serine ester I. As with the Scheme 3

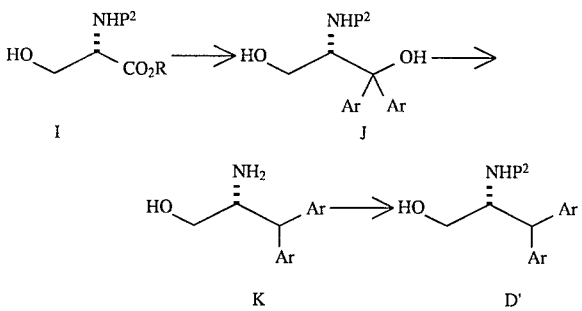

other serine esters described above, the ester "R" group is typically an alkyl group having from 1 to 10 carbon atoms or arylalkyl group having from 5 to 12 carbon atoms and, preferably, is methyl, ethyl or benzyl. The N-protected serine ester is chosen such that the $P^2$ protecting group may be cleaved under reducing conditions (e.g., $P^2$ is a CBZ or FMOC group). The N-protected serine esters I may be readily prepared from the corresponding serine ester hydrochloride by using standard protecting group chemistry (e.g., reaction with fluorenylmethoxycarbonyl-N-hydroxysuccinimide (FMOC-ONSu) or carbobenzyloxy chloride (CBZ-$C_l$)). As with the synthetic approaches shown in Schemes 1 and 2, the approach depicted in Scheme 3 may be carried out using racemic or optically active starting material.

Treatment of N-protected serine ester I with an aryl metal reagent produces N-protected diarylaminopropanediol J. Reaction of diarylaminopropanediol J with a reducing agent results in both deoxygenation of the benzylic alcohol and removal of the protecting group $P^2$. Preferably the protecting group $P^1$ on aminopropanediol J is a carbobenzyloxy group (CBZ) and the reducing agent is a dissolving metal such as sodium or lithium. The dissolving metal reduction may be carried out in a solvent which includes liquid ammonia and a cosolvent such as tetrahydrofuran. If a hydrogen source is employed as the reducing agent, the reaction is preferably carried out in the presence of a palladium catalyst (e.g., 10% Pd/C).

The resulting diarylaminopropanol K may be converted into N-protected diarylaminopropanol D' using standard methods for the introduction of protecting groups. For example, the aminoalcohol may be treated with FMOC-ONSu to form N-FMOC diarylaminopropanol D'.

The invention will be further characterized by the following examples. These examples are not meant to limit the scope of the invention which has been fully set forth in the foregoing description. Variation within the concepts of the invention as described herein will be apparent to those skilled in the art.

Scheme 4 shows a six step sequence used for the synthesis of (R)-diphenylalanine and three analogs starting from the ester of a naturally occurring amino acid, (S)-serine, or the corresponding analogs. Examples 1–6 contain descriptions of the individual reactions. The synthesis of the diphenylalanines via this route is simple, requires no chromatographic purification, and may be run on a large scale.

Scheme 4

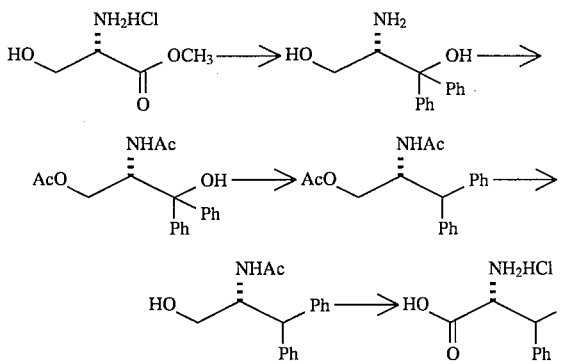

EXAMPLE 1

Grignard Reactions with Serine Methyl Ester Hydrochloride

Grignard reagent was either purchased from a commercial source (Aldrich Chemical Company, Milwaukee, Wis.) or prepared in situ from the corresponding aryl bromide. For in situ preparation, the bromide (193.54 mmol) was added to magnesium turnings (193.54 mmol) over 45 min in diethyl ether at room temperature at such a rate that the ether mildly refluxed. After complete addition, the reaction was stirred at room temperature (2–2.5 h) until the magnesium was consumed. The resulting reagent was then transferred to an addition funnel and added dropwise to (S)-serine methyl ester hydrochloride (32.25 mmol) in diethyl ether at room temperature. The reaction was stirred at room temperature for 12 to 24 h and was quenched with 3M aqueous HCl (~250 ml) or until pH was 2. The aqueous phase was separated and washed with methylene chloride (CH$_2$Cl$_2$; 3×100 ml) and the organic washes were discarded. The aqueous phase was adjusted to pH 11–12 and then extracted with methylene chloride. The combined organic extracts were washed with water, brine, and dried over MgSO$_4$ and the solvent removed under vacuum to afford the respective (S)-diarylaminopropanediols, which did not require further purification.

Yields: R=H—57%
R=CH$_3$—42%
R=F—64%
R=OCH$_3$—26%

EXAMPLE 2

Diacetylation with Acetic Anhydride

To a pre-cooled solution of (S)-diarylaminopropanediol (8.60 mmol; prepared according to Example 1) in pyridine (30.10 mmol) and CH$_2$Cl$_2$ (20 ml) was added acetic anhydride (25.80 mmol) dropwise over 10 minutes. The reaction mixture was then stirred for 2 h. The reaction progress was monitored by thin layer chromatography (TLC). Upon completion, the reaction mixture was diluted with CH$_2$Cl$_2$ and washed with 3M aqueous HCl (100 ml). The two phases were separated and the aqueous phase was re-extracted with CH$_2$Cl$_2$ (2×50 ml). The combined organic extracts were washed with water, brine, and dried over MgSO$_4$. Concentration under vacuum furnished the respective (S)-diacetate in quantitative yield. The diacetates were further purified by recrystallization using ethyl acetate and hexane. The yields for the diacetates obtained after recrystallization are shown below.

Yields: R=H—73%
R=CH$_3$—81%
R=F—87%
R=OCH$_3$—74%

EXAMPLE 3

Deoxygenation

To an (S)-diacetate prepared according to Example 2 (2.75 mmol) in CH$_3$COOH (10 ml) was added ammonium formate (13.77 mmol) followed by Pd-C (10% Pd) (15% of the weight of the diacetate). The reaction mixture was then lowered into an oil bath pre-heated to 120° C. The reaction was stirred at reflux for 2 to 6 h and monitored by TLC. Upon completion, the mixture was cooled and diluted with CH$_2$Cl$_2$, and filtered over a small bed of celite. The filtrate was washed with water, aqueous sodium bicarbonate (NaHCO$_3$) solution, and brine. The organic layer was dried over anhydrous magnesium sulfate (MgSO$_4$) and concentrated under vacuum affording a solid diacetylated (R)-diarylaminopropanol which was used in the next reaction without further purification.

Yields: R=H—74%
R=CH$_3$—100%
R=F—90%
R=OCH$_3$—100%

EXAMPLE 4

Mono-deacetylation using Guanidine

To a diacetylated (R)-diarylaminopropanol (5.6 mmol) prepared according to Example 3 in CH$_2$Cl$_2$ (5 ml) was added 1M solution of guanidine (11.2 mmol, 11.2 ml) in EtOH. The reaction progress was monitored by TLC. Upon completion, solvent was evaporated and the residue was dissolved in CH$_2$Cl$_2$ (50 ml). The resulting organic layer was washed with water and brine. The organic layer was dried over anhydrous MgSO$_4$ and solvent was evaporated yielding the respective N-acetyl (R)-diaryl-aminopropanol as a white solid. The N-acetyl diarylaminopropanols were used without further purification.

Yields: R=H—82%
R=CH$_3$—100%
R=F—93%
R=OCH$_3$—86%

EXAMPLE 5

Oxidation of N-Acetyl Diarylaminopropanols with Chromium Trioxide

To an N-acetyl (R)-diarylaminopropanol (2.02 mmol; prepared according to Example 4) in acetone (10 ml) was added Jones reagent (prepared according to Organic Synthesis, Vol. 5, p. 310) dropwise at room temperature until the reaction turned red. The reaction was monitored by TLC.

After completion, isopropanol was added to quench the excess Jones reagent or until the reaction color turned green. The solvent was decanted to separate the chromium salts. The residue was washed with acetone (2×20 ml) and again decanted. The combined supernatants were concentrated under vacuum and the residue dissolved in $CH_2Cl_2$ (50 ml). The organic layer was washed with water to remove any chromium impurities. Further purification via acid/base extraction furnished the desired N-acetyl (R)-diarylalanine as a white solid.

Yields: R=H—88%
R=$CH_3$—97%
R=F—91%
R=$OCH_3$—27[{]jf44a

EXAMPLE 6

Deacetylation with Hydrochloric Acid

An N-acetyl (R)-diarylalanine prepared according to Example 5 (1.0 mmol) in 6M aqueous HCl was heated to reflux for 3 to 9 hr or until the starting material had completely dissolved. The reaction mixture was then cooled and water was removed under vacuum to afford the hydrochloride salt of the respective (R)-diarylalanine in high yield. The amine hydrochlorides were further purified by recrystallization.

Yields: R=H—96%
R=$CH_3$—100%
R=F—100%
R=$OCH_3$70%

Scheme 5 shows an alternative sequence employed for the preparation of N-BOC-(R)-diphenylalanine starting from (S)-serine methyl ester (L-serine methyl ester). Examples 7 and 10–14 contain descriptions of the individual reactions depicted in Scheme 5. Examples 8 and 9 report the preparation of (S)-4-(hydroxydiphenylmethyl)-2-oxazolidinone from (S)-3-hydroxydiphenylalaninol (the preparation of which is described in Example 1) via an alternative approach.

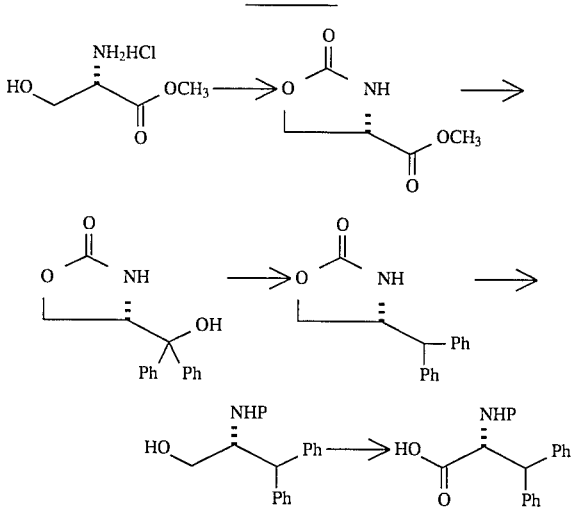

Scheme 5

EXAMPLE 7

(S)-4-Carbomethoxy-2-oxazolidinone

To (S)-serine methyl ester hydrochloride (20 g, 128.64 mmol) in water (230 ml) was added $KHCO_3$ (14.16 g, 141.52 mmol) and $K_2CO_3$ (19.56 g, 141.52 mmol) at room temperature. It was then cooled by an ice bath and triphosgene (19.04 gm, 64.32 mmol) was added in toluene (192 ml) via an addition funnel over 25 minutes. The reaction mixture turned cloudy. After 2 h, reaction phases were separated and the aqueous layer was lyophilized to yield (S)-4-carbomethoxy-2-oxazolidinone as a white solid (16.5 g) in 88% yield.

EXAMPLE 8

(S)-4-(hydroxyethyldiphenyl-2-oxazolidinone

Phenyl magnesium bromide was prepared by slow addition of bromobenzene (14.53 ml, 137.93 ml) in THF (50 ml) to Mg (3.31 g, 137.93 g atom). The reaction mixture was stirred for one hour or until most of the Mg had been consumed. (S)-Carbomethoxy oxazolidinone (5 g, 34.48 mmol; prepared according to Example 7), dissolved in THF (25 ml), was added dropwise over 15 min period and allowed to stir an additional hour. The reaction mixture was then cooled with an ice bath and aqueous 2M HCl (85 ml) was added dropwise which resulted in the formation of crystals. The reaction mixture was transferred to a 500 ml round bottom flask aided with 100 ml EtOAc and the organics were evaporated. Aqueous $Na_2SO_3$ (30 ml) was added along with 100 ml hexane. The mixture was shaken and the white crystals were filtered. Crystals were washed with hexane (50 ml) to remove biproduct and dried to furnish the desired (S)-hydroxymethyldiphenyloxazolidinone (6.79 g) in 73% yield. mp: 227°–230° C., $[\alpha]_D^{25}$=−14.85, (C=1.3, DMSO).

EXAMPLE 9

(S)-4-(Hydroxyphenylmethyl)-2-oxazolidinone

To (S)-3-hydroxydiphenylalaninol (40 g, 164.61 mmol; prepared according to Example 1), anhydrous $K_2CO_3$ (2.3 g, 16.46 mmol) was added diethyl carbonate (50 ml, 411.52 mmol). The reaction mixture was lowered into an oil bath preheated to 135° C., and was stirred until 46 ml EtOH was collected as the distillate. The oil bath was removed upon cessation of EtOH distillation and the reaction mixture was cooled and $CH_2Cl_2$ (750 ml) was added. The reaction mixture was transferred to a separatory funnel, and the organics were washed with water (750 ml). The organic phase was dried over $MgSO_4$ and concentrated on a rotavap to furnish the desired (S)-hydroxydiphenylmethyloxazolidinone (43 g) in 93% yield.

EXAMPLE 10

(S)-4-(Hydroxydiphenylmethyl)-2-oxazolidinone

To a mixture of (S)-3-hydroxydiphenylalaninol (2.43 g, 10.00 mmol; prepared according to Example 1), $Et_3N$ (8.34 ml, 60.00 mmol) in $CH_2Cl_2$ (30 ml) was added triphosgene (0.98 g, 3.3 mmol) in $CH_2Cl_2$ (5 ml) at 0° C. The reaction mixture was stirred for 30 min. and diluted with $CH_2Cl_2$ (50 ml). The organic phase was washed with water (50 ml) and dried over $MgSO_4$ and subsequent concentration in vacuum afforded the desired (S)-hydroxydiphenylmethyloxazolidinone (2.6 g) in 92% yield.

EXAMPLE 11

(R)-4-(Methyldiphenyl)-2-oxazolidinone

To the (S)-hydroxydiphenylmethyloxazolidinone (5 g, 18.59 mmol; prepared according to Example 8, 9 or 10) in freshly distilled ammonia (250 ml) was added Na metal (1.28 g, 55.77 g atom) in intervals. The reaction mixture was stirred for 2 h at −33° C. Ammonia was evaporated and MeOH (20 ml) was added to the white residue. The residue was treated with 1M aqueous HCl (~100 ml). The organics were extracted with $CH_2Cl_2$ (3×50 ml). The combined organic extracts were washed with water and brine successively. Drying over anhydrous $MgSO_4$ and concentration in vacuum afforded a yellowish mass, which upon crystallization in EtOH gave the desired (R)-methyldiphenyloxazolidinone (3.32 g) in 70% yield. mp: 128°–130° C., $[\alpha]_D^{25}$=+25.70, (C=2.0, $CH_2Cl_2$).

EXAMPLE 12

(R)-N-(tert-Butyloxycarbonyl)-4-(methyldiphenyl)-2-oxazolidinone

To a premixed solution of (R)-methyldiphenyloxazolidinone (1.00 g, 3.95 mmol; prepared according to Example 11), BOC-anhydride (1.03 g, 4.74 mmol) and dimethylaminopyridine (DMAP; catalytic) in $CH_2Cl_2$ (10 ml) was added $Et_3N$ (0.715 ml, 5.14 mmol) at room temperature. The reaction mixture was worked up after 30 min. by addition of water (50 ml) and extraction of the aqueous layer with $CH_2Cl_2$ (3×20 ml). The combined organic extracts were washed with water and brine. Drying over $MgSO_4$ followed by concentration in vacuum afforded a white solid, which was then dissolved in EtOAc. Addition of hexane to the organic solution precipitated the desired (R)-methyldiphenyloxazolidinone as a white solid (1.12 g) in 80% yield. mp: 103°–105° C., $[\alpha]_D^{25}$ −30.90 (C=1.0, $CH_2Cl_2$).

EXAMPLE 13

(R)-2-N-(tert-Butyloxycarbonyl)-3,3-diphenyl-1-propanol

Cesium carbonate (0.178 g, 0.55 mmol) was added to the methanolic solution (40 ml) of N-BOC (R)-methyldiphenyloxazolidinone (1.964 g, 2.73 mmol; prepared according to Example 12). The reaction mixture was stirred for 2.5 h at room temperature and then quenched with solid citric acid (90.155 g, 0.55 mmol). Methanol was evaporated in vacuum. The crude solid was then dissolved in $CH_2Cl_2$ (30 ml) and the organic layer was washed with water and brine and dried over $MgSO_4$. Concentration on a rotavap afforded N-BOC (R)-diphenylalaninol as a white solid in 90% yield which needed no purification, but was chromatographed for analytical purposes (0.611 g, 88% yield). mp: 150°–152° C., $[\alpha]D^{25}$=−36.2 (C=1.0, MeOH).

EXAMPLE 14

(R)-N-(tert-butyloxycarbonyl)-diphenylalanine

Jones reagent (chromium trioxide in sulfuric acid and water) was added to N-BOC-(R)-diphenylalaninol (0.255 g, 1.0 mmol; prepared according to Example 13) in acetone (10 ml) until the reaction mixture retained a red color. The reaction mixture was then quenched with addition of isopropanol. The precipitated chromium salts were filtered through a pad of celite. The filtrate was concentrated on a rotavap. The resultant was dissolved in EtOAc (20 ml) and the organic layer was washed with water. Acid base extraction yielded N-BOC-(R)-diphenylalanine as a white powder (0.217 gm) in 80% yield. mp: 150°–152° C.; lit. 153° C., $[\alpha]_D^{25}$=−36.2 (C=1.0, MeOH); lit. $[\alpha]_D^{25}$ −35.7 (C=1.0, MeOH).

Scheme 6 shows an alternative five step sequence employed for the preparation of N-FMOC-(R)-diphenylalanine starting from L-serine methyl ester hydrochloride. Examples 15–19 contain descriptions of the individual reactions depicted in Scheme 6.

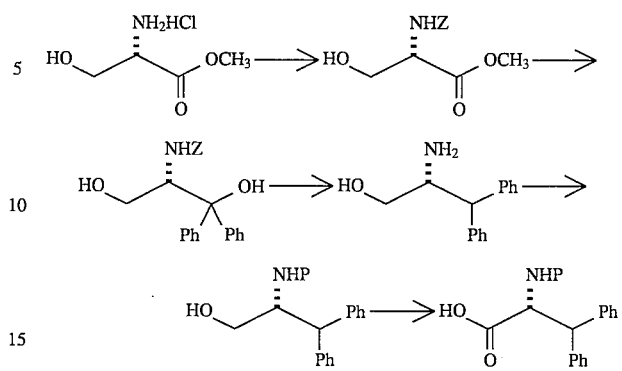

Scheme 6

EXAMPLE 15

(S)-N-(Benzyloxycarbonyl)-serine methyl ester

To (S)-serine methyl ester hydrochloride (70 g, 0.45 mol) in water (850 ml) was added $NaHCO_3$ (125.2 g, 1.49 mol) slowly. The mixture was stirred at room temperature for 15 min. and benzyloxycarbonyl chloride (77 ml, 0.54 mol) was added via an addition funnel. The reaction was stirred for an additional 12 h. The reaction mixture was extracted with $CH_2Cl_2$ (3×300 ml). The organic layer was dried over $MgSO_4$ and concentrated in vacuum to give N-Z-(S)-serine methyl ester as an oil (113.9 g) in yield, which solidified upon cooling in the refrigerator. $[\alpha]_D^{25}$=−13.78° (C=1.32, MeOH).

EXAMPLE 16

(S)-2-N-(Benzyloxycarbonyl)-2,2-diphenyl-1,3-propanediol

Phenyl magnesium bromide was prepared by addition of bromobenzene (209 ml, 1.98 mol) in $Et_2O$ (300 ml) at 0° C. to Mg metal (48 g, 1.98 g atom) in $Et_2O$ (500 ml). To this red solution was added N-Z-(S)-serine methyl ester 800 in ether (114 g, 0.45 mol) via an addition funnel at 0° C. The reaction was stirred for an additional 12 hr and quenched with 250 ml of conc. HCl in ice (~1 kg). The entire mass was extracted with EtOAc (3×100 ml). The combined organic phase was washed with water followed by brine. Drying over $MgSO_4$ and concentration in vacuum afforded the desired N-Z-(S)-diphenylaminopropanediol as a solid. The solid was further purified by recrystallization using EtOAc and hexane to yield (127.94 g; 75%) of the desired product.

EXAMPLE 17

(R)-Diphenylalaninol

To N-Z-(S)-diphenylaminopropanediol (24 g, 98.76 mmol) in freshly distilled $NH_3$ (700 ml) was added Na metal (6.814 g, 296.3 g atom) in intervals over 2.5 h. The reaction mixture was then quenched with solid $NH_4Cl$ (21 g) and $NH_3$ was allowed to evaporate and quenched with 1M HCl. The resulting white residue was extracted with $CH_2Cl_2$ (3×100 ml) and the combined organic phase was washed with water followed by brine. Drying over $MgSO_4$ and concentration in vacuum afforded (R)-diphenylalaninol as a solid (21 g) in quantitative yield. Further crystallization using EtOAc afforded a white powder (17 g) in 82% yield. mp: 108°–111° C., $[\alpha]_D^{25}$=−42.66 (C=1.35, $CH_2Cl_2$).

EXAMPLE 18

(R)-N-(9-Fluorenylmethoxycarbonyl)-diphenylalaninol

To (R)-diphenylalaninol (8.3 g, 36.56 mmol) in aqueous THF (1:9, v/v, 180 ml) was added 9-fluorenylmethoxycarbonyl-N-hydroxysuccinimide (FMOC-ONSu; 11.09 g, 32.90 mmol) and the reaction mixture was stirred at room temperature for 12 h. The reaction mixture was extracted with EtOAc (3×50 ml) and the two phases were separated. The combined organic phases were washed successively with 1M aqueous HCl (50 ml), water, then with brine, and dried over $MgSO_4$. Concentration in vacuum afforded N-FMOC-(R)-diphenylalaninol as a pale yellow solid (14.3 g) in 96% yield (based on the quantity of FMOC-ONSu used) which was used without further purification. The unreacted (R)-diphenylalaninol was recovered by acidification of the aqueous layer (0.8 g).

EXAMPLE 19

(R)-N-(9-Fluorenylmethoxycarbonyl)-diphenylalanine

The Jones reagent ($CrO_3$ in $H_2SO_4$ and water) was added dropwise at room temperature to a solution of N-FMOC-(R)-diphenylalaninol (14.4 g, 31.84 mmol) in acetone (140 ml) until the solution attained red color. The reaction mixture was quenched with addition of isopropanol. The precipitated chromium salts were filtered through a pad of celite and filtrate was concentrated in vacuum. To this green residue was added $CH_2Cl_2$ (300 ml) and the organic layer was washed with water to remove chromium impurities. The two phases were separated and organic phase was concentrated in vacuum. The residue was treated with dilute aqueous $NH_4OH$ solution (150 ml) and was washed with ether (3×50 ml). The two phases were separated and the aqueous layer was acidified with 1M aqueous HCl until pH 2. The precipitated solid was then extracted with $CH_2Cl_2$ (3 ×100 ml) and the combined organic extracts were washed with water followed by brine and dried over $MgSO_4$. Concentration in vacuum yielded a white solid which was further purified by trituration using $CH_2C_{12}$-hexane solvent system to afford N-FMOC-(R)-diphenylalanine as a white powder (10.7 g) in 724 yield. mp: 103°–105° C., $[\alpha]_D^{25}$– 15.4 (C=1.6, $CH_2Cl_2$)

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method for preparing a diarylalanine compound comprising the step of:

reacting a diarylaminopropanediol compound represented by the formula:

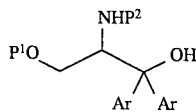

with a reducing agent to form a diarylaminopropanol compound represented by the formula:

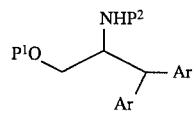

wherein Ar is a substituted or unsubstituted aromatic group; and $P^1$ and $P^2$ together are >C=O or $P^1$ is hydrogen or —C(O)$R^1$, where $R^1$ is a substituted or unsubstituted $C_3$–$C_7$ alkyl group, a substituted or unsubstituted $C_3$–$C_7$ cycloalkyl group, a substituted or unsubstituted arylalkyl group, or a substituted or unsubstituted phenyl group; and $P^2$ is hydrogen, —C(O)$R^2$, or —C(O)O$R^3$, wherein $R^2$ is hydrogen, a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group, and $R^3$ is a substituted or unsubstituted $C_1$–$C_{10}$ alkyl group, a substituted or unsubstituted $C_3$–$C_7$ cycloalkyl group, a substituted or unsubstituted arylalkyl group, a substituted or unsubstituted phenyl group, a substituted or unsubstituted fluorenyl group, a substituted or unsubstituted allyl group.

2. A method for preparing a diarylmethyloxazolidinone comprising the step of:

reacting a diarylhydroxymethyloxazolidinone compound represented by the formula:

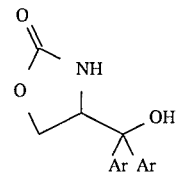

with a reducing agent to form a diarylmethyloxazolidinone compound represented by the formula:

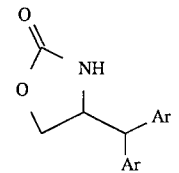

wherein Ar is a substituted or unsubstituted aromatic group.

3. A method for preparing a diarylalanine compound comprising:

(a) reacting an aryl metal reagent with a serine ester compound represented by the formula:

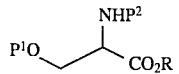

wherein R is a $C_1$–$C_{10}$ alkyl group;

$P^1$ and $P^2$ together are C(O) or $P^1$ is hydrogen or —C(O)$R^1$, where $R^1$ is a substituted or unsubstituted $C_1$–$C_{10}$ alkyl group, a substituted or unsubstituted benzyl group, or a substituted or unsubstituted phenyl group; and $P^2$ is —H.HCl, —C(O)$R^2$, or —C(O)O$R^3$, wherein $R^2$ is hydrogen, a substituted or unsubstituted $C_1$–$C_{10}$ alkyl group, a substituted or unsubstituted benzyl group, or a substituted or unsubstituted phenyl group, and $R^3$ is a substituted or unsubstituted $C_1$–$C_{10}$ alkyl group, a substituted or unsubstituted benzyl group, or a substituted or unsubstituted fluorenyl group;

to form a diarylaminopropanediol compound represented by the formula:

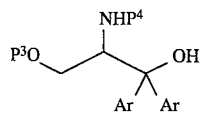

wherein Ar is a substituted or unsubstituted aromatic group;

$P^3$ and $P^4$ together are >C(O), or $P^3$ is hydrogen or —C(O)$R^1$; and $P^4$ is hydrogen, —C(O)$R^2$ or —C(O)O$R^3$; and (b) reacting a diarylaminopropanediol compound represented by the formula:

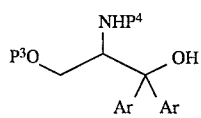

with a reducing agent to form a diarylaminopropanol compound represented by the formula:

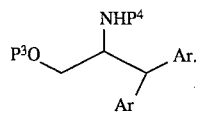

4. The method of claim 3 comprising reacting a diarylaminopropanediol compound represented by the formula:

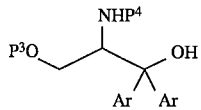

wherein $P^3$ is hydrogen or —C(O)$R^1$, where $R^1$ is a $C_1$–$C_6$ alkyl group; and $P^4$ is —C(O)$R^2$ or —C(O)O$R^3$, wherein $R^2$ is a $C_1$–$C_6$ alkyl group, and $R^3$ is a $C_1$–$C_6$ alkyl group or a benzyl group, with a hydrogen source in the presence of a palladium catalyst to form a diarylaminopropanol compound represented by the formula:

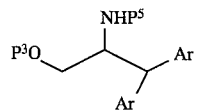

wherein $P^5$ is hydrogen, —C(O)$R^2$ or —C(O)O$R^4$, wherein $R^4$ is a $C_1$–$C_6$ alkyl group.

5. The method of claim 3 comprising:

reacting an aryl magnesium halide with a serine ester compound represented by the formula:

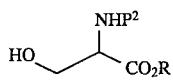

to form a diarylaminopropanediol compound represented by the formula:

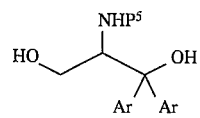

wherein $P^5$ is hydrogen, —C(O)$R^2$ or —C(O)O$R^3$.

6. The method of claim 3 comprising:

(a) treating an (S)-serine ester hydrochloride compound represented by the formula:

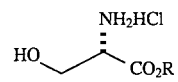

wherein R is a $C_1$–$C_6$ alkyl group;

with a phenyl magnesium halide, a methylphenyl magnesium halide, a methoxyphenyl magnesium halide, or a fluorophenyl magnesium halide, to form an (S)-diarylaminopropanediol compound represented by the formula:

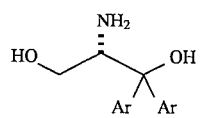

wherein Ar- is phenyl, methylphenyl, methoxyphenyl or fluorophenyl; and (b) reacting a protected (S)-diaryl-aminopropanediol represented by the formula:

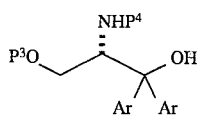

wherein $P^3$ is hydrogen or —C(O)$R^1$, where $R^1$ is a $C_1$–$C_6$ alkyl group; and $P^4$ is —C(O)$R^2$, and $R^2$ is a $C_1$–$C_6$ alkyl group;

with a hydrogen source in the presence of a palladium catalyst to form an N-protected (R)-diarylaminopropanol represented by the formula:

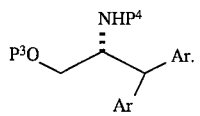

7. A method for preparing a diarylalanine compound comprising:

(a) reacting an aryl metal reagent with a serine ester compound represented by the formula:

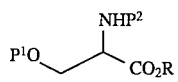

to form a diarylaminopropanediol compound represented by the formula:

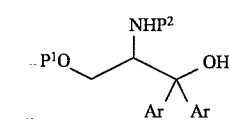

wherein R is a $C_1$–$C_{10}$ alkyl group; Ar is a substituted or unsubstituted aromatic group; and $P^1$ and $P^2$ together are

>C=O or $P^1$ is hydrogen or —C(O)$R^1$, where $R^1$ is a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group; and $P^2$ is —H.HX, —C(O)$R^2$ or —C(O)O$R^3$, wherein X is chlorine or bromine, $R^2$ is hydrogen, a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group, and $R^3$ is a substituted or unsubstituted $C_1$–$C_{10}$ alkyl group, a substituted or unsubstituted $C_3$–$C_7$ cycloalkyl group, a substituted or unsubstituted arylalkyl group, a substituted or unsubstituted phenyl group, a substituted or unsubstituted fluorenyl group, or a substituted or unsubstituted allyl group; and (b) reacting a diarylaminopropanediol compound represented by the formula:

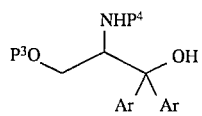

with a reducing agent to form a diarylaminopropanol compound represented by the formula:

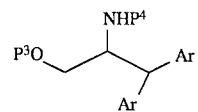

wherein Ar is a substituted or unsubstituted aromatic group; and $P^3$ and $P^4$ together are

>C=O or $P^3$ is hydrogen or —C(O)$R^4$ where $R^4$ is a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group; and $P^4$ is hydrogen, —C(O)$R^5$, or —C(O)O$R^6$, wherein $R^5$ is hydrogen, a substituted or unsubstituted $C_1$–$C_{10}$ alkyl group, a substituted or unsubstituted $C_3$–$C_7$ cycloalkyl group, a substituted or unsubstituted arylalkyl group, or a substituted or unsubstituted phenyl group, and $R^6$ is a substituted or unsubstituted $C_1$–$C_{10}$ alkyl group, a substituted or unsubstituted $C_3$–$C_7$ cycloalkyl group, a substituted or unsubstituted arylalkyl group, a substituted or unsubstituted phenyl group, a substituted or unsubstituted fluorenyl group, or a substituted or unsubstituted allyl group.

8. The method of claim 7 comprising reacting a protected diarylaminopropanediol compound represented by the formula:

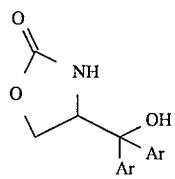

with sodium in the presence of liquid ammonia to form a protected diarylaminopropanol compound represented by the formula:

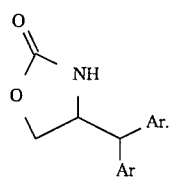

9. The method of claim 8 further comprising the steps of:

i) reacting the protected diarylaminopropanol compound with BOC-anhydride in the presence of a base to form an N-BOC-oxazolidinone compound represented by the formula:

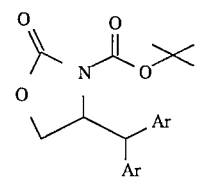

and ii) contacting the N-BOC-oxazolidinone compound with cesium carbonate in the presence of an alcohol to form an N-protected diarylaminopropanol compound represented by the formula:

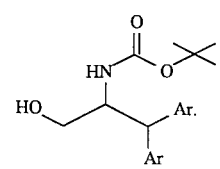

10. The method of claim 7 comprising reacting a diarylaminopropanediol compound represented by the formula:

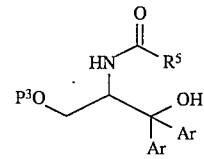

with a hydrogen source in the presence of a palladium catalyst to form a diarylaminopropanol compound represented by the formula:

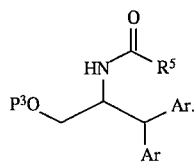

11. The method of claim 10 further comprising the step of reacting the diarylaminopropanol compound, wherein P³ is —C(O)R⁴, with a deprotecting agent to form an N-protected diarylaminopropanol compound represented by the formula:

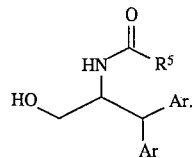

12. The method of claim 7 comprising reacting a diarylaminopropanediol compound represented by the formula:

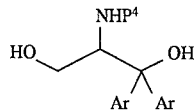

wherein P⁴ is —C(O)OR⁶ and R⁶ is a substituted or unsubstituted benzyl group, or a substituted or unsubstituted fluorenyl group, with the reducing agent to form a diarylaminopropanol compound represented by the formula:

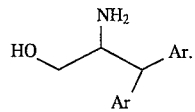

13. The method of claim 7 comprising reacting the diarylaminopropanediol compound with sodium in the presence of ammonia to form the diarylaminopropanol compound.

14. The method of claim 7 comprising reacting the diarylaminopropanediol compound with a hydrogen source in the presence of a palladium catalyst to form the diarylaminopropanol compound.

15. The method of claim 7 further comprising the step of reacting an N-protected diarylaminopropanol compound represented by the formula:

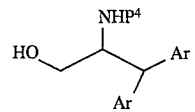

wherein P⁴ is —C(O)R⁵ or —C(O)OR⁶, with an oxidizing agent to form an N-protected diarylalanine compound represented by the formula:

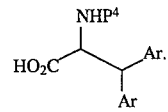

16. The method of claim 15 wherein the oxidizing agent includes H₂CrO₄ or oxygen.

17. The method of claim 15 further comprising the step of reacting the N-protected diarylalanine compound with a deprotecting agent to form a diarylalanine compound represented by the formula:

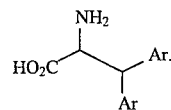

18. The method of claim 17 wherein reacting the N-protected diarylalanine compound with the deprotecting agent comprises reacting the N-protected diarylalanine compound with an aqueous solution of hydrochloric acid.

19. The method of claim 7 further comprising the step of reacting the diarylaminopropanol compound, wherein P³ is —C(O)R⁴ and P⁴ is —C(O)R⁵ or —C(O)OR⁶, with a deprotecting agent to form an N-protected diarylaminopropanol compound represented by the formula:

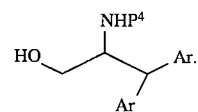

20. The method of claim 7 further comprising the step of reacting the diarylaminopropanol compound represented by the formula:

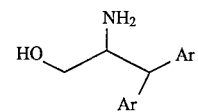

with a derivatizing agent to form an N-protected diarylaminopropanol compound represented by the formula:

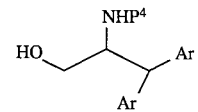

wherein P⁴ is —C(O)R⁵ or —C(O)OR⁶.

21. The method of claim 7 wherein the aryl metal reagent includes a compound selected from the group consisting of an aryl magnesium chloride, an aryl magnesium bromide and an aryl magnesium iodide.

22. The method of claim 7 further comprising the steps of:

a) treating an (S)-serine ester hydrochloride compound represented by the formula:

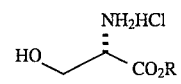

wherein R is a C₁–C₆ alkyl group, with an ArMgX compound, wherein Ar is phenyl, methylphenyl, methoxyphenyl, or fluorophenyl and X is chlorine, bromine, or iodine; to form an (S)-diarylaminopropanediol compound represented by the formula:

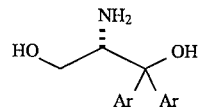

b) contacting the (S)-diarylaminopropanediol compound with a derivatizing agent to form a protected (S)-diarylaminopropanediol represented by the formula:

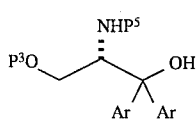

wherein $P^3$ is hydrogen or $-C(O)R^4$, and $P^5$ is $-C(O)R^4$.

23. The method of claim 22 comprising reacting the protected (S)-diarylaminopropanediol with a hydrogen source in the presence of a palladium catalyst to form a protected (R)-diarylaminopropanol represented by the formula:

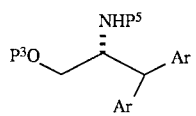

and further comprising reacting an N-protected (R)-diarylaminopropanol represented by the formula:

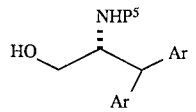

with an oxidizing agent to form an N-protected (R)-diarylalanine represented by the formula:

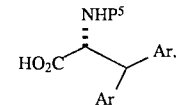

24. The method of claim 7 comprising the step of:
contacting a protected serine ester compound represented by the formula:

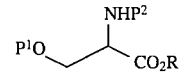

wherein R is a $C_1$–$C_6$ alkyl group, and $P^1$ and $P^2$ together are

>C=O or
$P^1$ is hydrogen or $-C(O)R^1$, where $R^1$ is an unsubstituted $C_1$–$C_{10}$ alkyl group, a benzyl group, or an unsubstituted phenyl group; and
$P^2$ is $-C(O)R^2$, or $-C(O)OR^3$, wherein $R^2$ is an unsubstituted $C_1$–$C_{10}$ alkyl group, a benzyl group, or an unsubstituted phenyl group, and $R^3$ is an unsubstituted $C_1$–$C_{10}$ alkyl group, a benzyl group, or an unsubstituted phenyl group;

with an aryl metal reagent to form a protected diarylaminopropanediol compound represented by the formula:

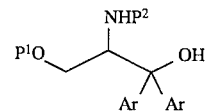

wherein Ar is a substituted or unsubstituted phenyl group.

25. The method of claim 7 comprising the step of:
contacting a serine ester hydrochloride compound represented by the formula:

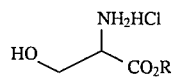

wherein R is a $C_1$–$C_{10}$ alkyl group, with an aryl metal reagent to form a diarylaminopropanediol compound represented by the formula:

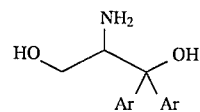

wherein Ar is an aromatic group selected from the group consisting of substituted and unsubstituted phenyl groups, and substituted and unsubstituted naphthyl groups.

26. The method of claim 25 comprising reacting an (R)-serine ester hydrochloride compound having the formula:

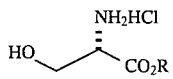

with an aryl magnesium bromide compound selected from the group consisting of phenyl magnesium bromide, methylphenyl magnesium bromide, methoxyphenyl magnesium bromide, and fluorophenyl magnesium bromide, to form an (R)-diarylaminopropanol represented by the formula:

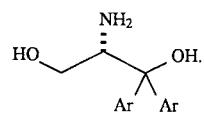

* * * * *

UNITED STATES PATENT AND TRADEMARK OFFICE
CERTIFICATE OF CORRECTION

PATENT NO. : 5,623,087

DATED : April 22, 1997

INVENTOR(S) : Sibi et al.

It is certified that error appears in the above-identified patent and that said Letters Patent is hereby corrected as shown below:

On title page, item

[56], References Cited, Other Publications: in the reference to Gage et al., "Oxazolidnone" should read --Oxazolidinone--

Col. 8, line 45: "(CBZ-C$_1$)" should read --(CBZ-C1))--

Col. 8, line 53: "P$^1$" should read --P$^2$--

Col. 11, line 15: delete "[{]jf44a" immediately after "R=OCH$_3$-27", and insert a "%" sign.

Col. 12, line 34: "Hydroxyphenylmethyl" should read --Hydroxydiphenylmethyl--

Col. 16, line 10, claim 1: "C$_3$-C$_7$" before "alkyl group" should read --C$_1$-C$_{10}$--

Col. 16, line 65, claim 3: "H.HCl" should read --H·HCl--

Col. 19, line 13, claim 7: "H.HX" should read --H·HX--

Col. 20, line 18, claim 8: delete the "." immediately after "Ar" in the formula

Col. 20, line 46, claim 9: delete the "." immediately after "Ar" in the formula

Col. 21, line 5, claim 10: delete the "." immediately after "Ar" in the formula

Col. 21, line 16, claim 11: delete the "." immediately after "Ar" in the formula Col. 21, line 34, claim 12: delete the "." immediately after "Ar" in the formula

UNITED STATES PATENT AND TRADEMARK OFFICE
CERTIFICATE OF CORRECTION

PATENT NO. : 5,623,087

DATED : April 22, 1997

INVENTOR(S) : Sibi et al.

It is certified that error appears in the above-identified patent and that said Letters Patent is hereby corrected as shown below:

Col. 21, line 60, claim 15: delete the "." immediately after "Ar" in the formula Col. 22, line 5, claim 17: delete the "." immediately after "Ar" in the formula Col. 22, line 21, claim 19: delete the "." immediately after "Ar" in the formula Col. 23, line 31, claim 23: delete the "." immediately after "Ar" in the formula Signed and Sealed this Second Day of December, 1997

*Attest:*

BRUCE LEHMAN

*Attesting Officer*   Commissioner of Patents and Trademarks